United States Patent [19]
Brooks

[11] Patent Number: 5,176,543
[45] Date of Patent: Jan. 5, 1993

[54] UNIVERSAL CONNECTOR APPARATUS
[75] Inventor: Robert J. Brooks, Mukilteo, Wash.
[73] Assignee: SpaceLabs, Inc., Redmond, Wash.
[21] Appl. No.: 851,982
[22] Filed: Mar. 12, 1992
[51] Int. Cl.⁵ .......................................... H01R 13/00
[52] U.S. Cl. .................................................. 439/859
[58] Field of Search ............... 439/816, 817, 859, 861, 439/862

[56] References Cited
U.S. PATENT DOCUMENTS

| | | | |
|---|---|---|---|
| 3,995,644 | 12/1976 | Parsons et al. | 439/859 |
| 4,094,571 | 6/1978 | Benjamin | 439/859 |
| 4,671,591 | 6/1987 | Archer | 439/859 |

Primary Examiner—Joseph H. McGlynn
Attorney, Agent, or Firm—Seed and Berry

[57] ABSTRACT

A cable connector is provided for mating with connectors of defibrillation electrodes made from various manufacturers. The connector includes a body having a lip portion for mechanically securing the connector to a defibrillation electrode having a cup-type connector. The body includes a spring mounted therein for mechanically securing the connector to a defibrillation electrode including a post. A retainer includes a post channel constructed with a dual diameter for accommodating the construction of both small and long posts of various defibrillation electrode connectors.

4 Claims, 4 Drawing Sheets

UNIVERSAL CONNECTOR APPARATUS

TECHNICAL FIELD

The present invention is directed toward a connector for electrically coupling a defibrillator to a defibrillation electrode and, more particularly, toward a universal connector allowing a defibrillator to be used with a variety of the most popular types of defibrillation electrodes.

BACKGROUND OF THE INVENTION

In the medical field, defibrillators and defibrillation electrodes have become commonplace. With particular reference to emergency care, portable defibrillators are now being used by mobile medical units to provide on-the-spot defibrillation to patients. Portable defibrillators are now being manufactured by several manufactures including Laerdal, SpaceLabs, and Physio-Control.

Portable defibrillators typically include a defibrillator unit for generating the electrical defibrillation signals to be transmitted to the patient. Portable defibrillators may also include additional medical monitoring capability for monitoring electrical signals from the patient indicating the patients condition, e.g., electrocardiogram (EKG). The portable defibrillators also include cables fixed to the defibrillators at one end and having a cable connector at the other end for mating with a defibrillator connector mounted on the defibrillation electrode. The defibrillation electrodes are secured on the chest of a patient generally by a layer of adhesive on the surface of the electrode. The electrode couples the defibrillation signal from the defibrillator cable to the patient.

Each defibrillator manufacture provides its own defibrillation electrode to be used in combination with its portable defibrillators. The defibrillator connectors on the defibrillation electrodes of the various manufacturers each have unique constructions so that only the cable connectors, and hence the defibrillators, of the manufacturers can be used in combination with the manufacturer's defibrillation electrode. As a result, the defibrillation electrodes used by the mobile medical team may not be compatible with the defibrillator equipment of a subsequent medical team operating on the patient during a subsequent time period.

As an example, in an emergency situation the first medical team to arrive may be a mobile medical team having their own portable defibrillator and will therefore affix defibrillation electrodes compatible with their portable defibrillator to the patient for defibrillation or other medical monitoring. However, the defibrillator of the mobile medical team may not be compatible with the defibrillator contained in an ambulance in which the patient is transported or a hospital where the patient arrives for initial treatment. Accordingly, the defibrillation electrodes of the mobile medical team must be removed from the patient so that defibrillation electrodes that are compatible with the ambulance and/or hospital defibrillator can be replaced therefor.

More importantly, the need to replace defibrillation electrodes so that subsequent defibrillation electrodes are compatible with the defibrillator equipment then being used may cause a dangerous delay in a required defibrillation. More specifically, defibrillation may be required during the time that a first set of defibrillation electrodes are being removed and a compatible set of defibrillation electrodes are being attached to the chest of the patient, thereby causing irreparable injury to the patient. Accordingly, it is desirable to provide apparatus for enabling medical equipment to be coupled to substantially any defibrillation electrode from any manufacturer.

SUMMARY OF THE INVENTION

The present invention provides a universal connector for coupling a defibrillator to defibrillation electrodes having a variety of connector structures. The connector includes a body for receiving electrical signals from the defibrillator and for transferring electrical signals to the defibrillator. The body includes a lip portion for mating with a cup connector of the defibrillation electrode. The connector also includes a spring for engaging a post of the defibrillation electrode and for transferring electrical signals between the post and the body. The body is constructed for receiving and positioning the spring so that the spring is proximate the post when the connector is mounted to the defibrillation electrode. The connector also includes a retainer for retaining the spring in the body. The retainer includes a channel for receiving a post of the defibrillation electrode wherein the channel extends through the retainer and wherein the channel includes first and second portions having respective first and second diameters, the first diameter being smaller than the second diameter. The connector also includes a casing for receiving the body, spring, and retainer. The casing includes a cable secured to the body for conducting electrical signals between the body and the defibrillator.

DETAILED DESCRIPTION OF THE INVENTION

Figure 1:
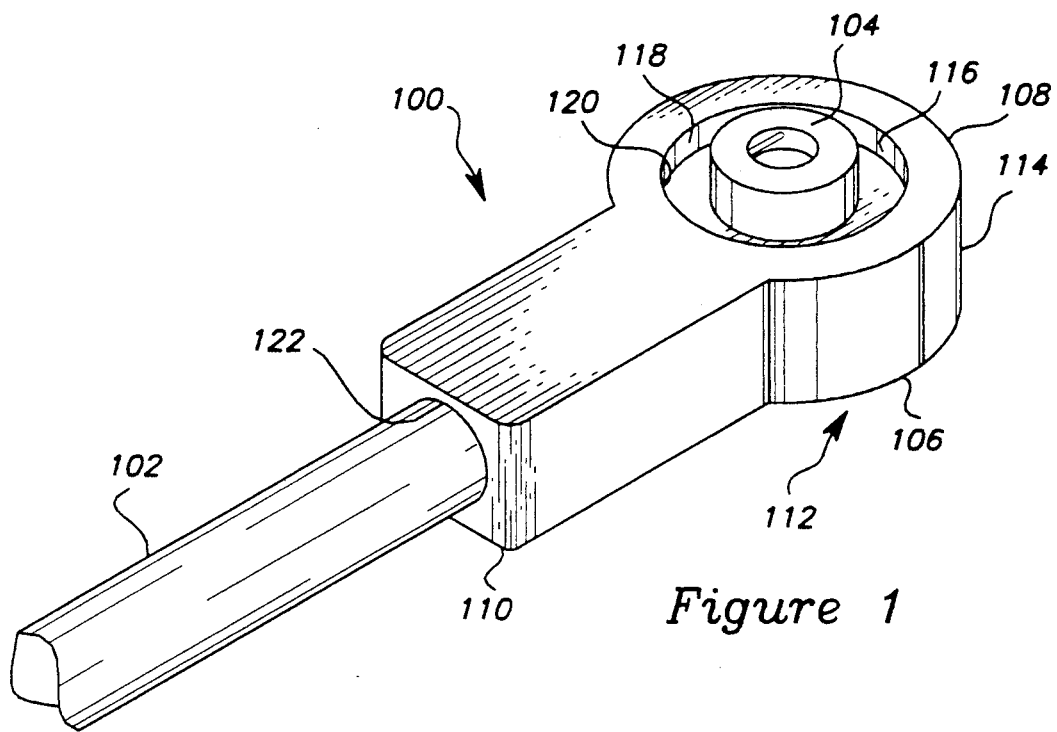
FIG. 1 is an isometric view of one embodiment of the connector of the present invention.
Figure 4A:
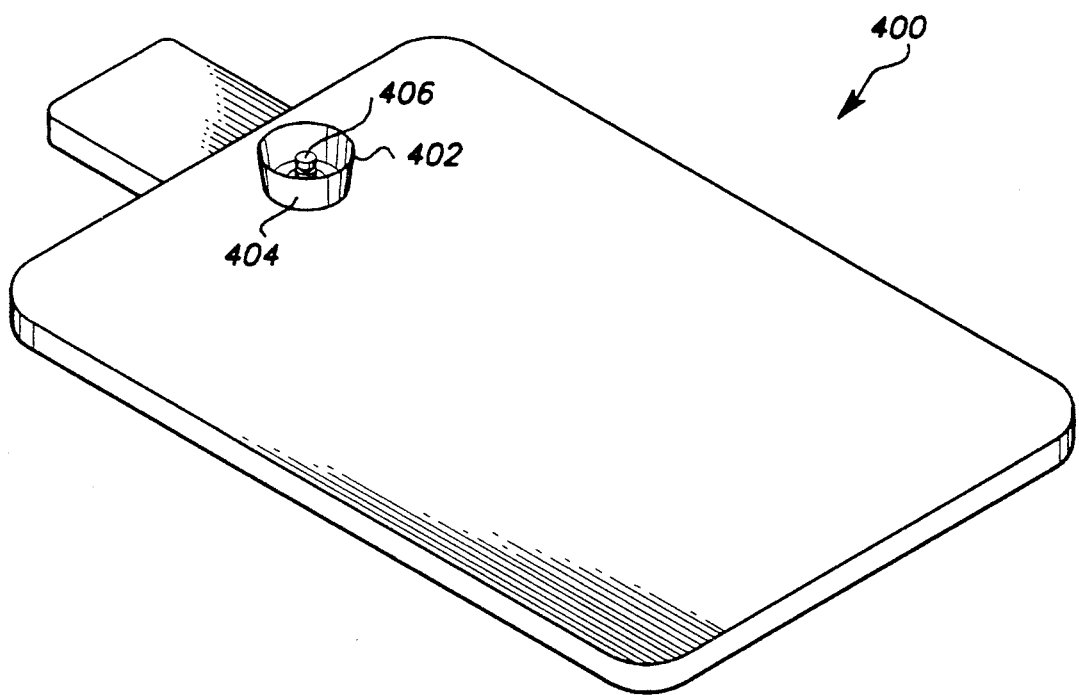
FIG. 4A is an isometric view of a defibrillation electrode for use with the connector of the subject invention.

FIG. 1 is an illustration of a connector 100 constructed for electrically coupling a defibrillator (not shown) to a defibrillation electrode, such as defibrillation electrode 400 illustrated in FIG. 4A. The defibrillation electrode 400 includes a defibrillator connector 402 constructed to electrically and mechanically mate with the connector 100 illustrated in FIG. 1.

Figure 4B:
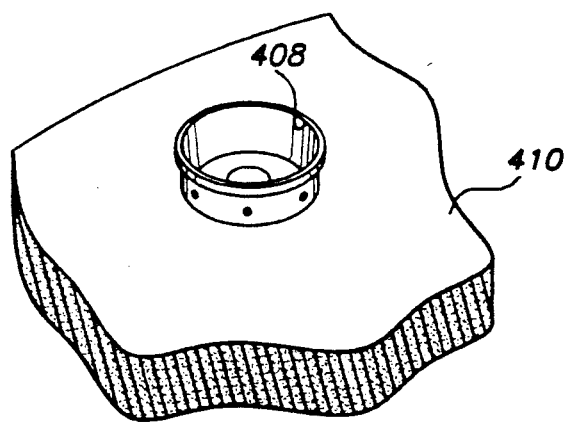
FIGS. 4B, 4C, and 4D are partial isometric views of other defibrillation electrodes for use with the connector of the subject invention.
Figure 4C:
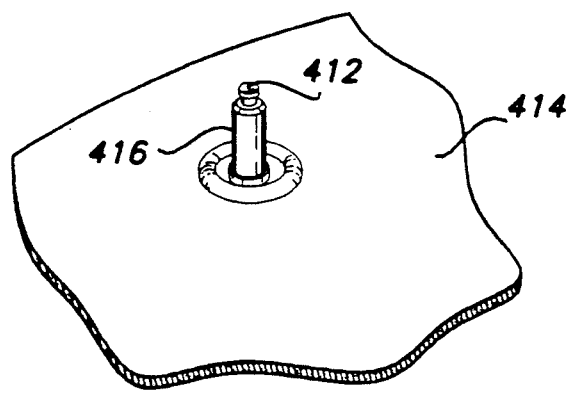

In accordance with the subject invention, the connector 100 is constructed to mate both electrically and mechanically with a variety of defibrillator connectors from a variety of manufacturers. More particularly, the defibrillator connector 402 illustrated in FIG. 4A is a post-type connector including a retention cup 404 and a small post 406. Post-type connectors including retention cups and small posts such as that illustrated in FIG. 4A are commercially available from the First Medic Company. Alternatively, the connector 100 is constructed for mating with a cup-type connector 408 of a defibrillation electrode 410 illustrated in FIG. 4B. Defibrillation electrodes having cup-type connectors as illustrated in FIG. 4B are available from the Laerdal Company. Still further, the connector 100 illustrated in FIG. 1 is constructed for mating with a connector post 412 of a defibrillation electrode 414 illustrated in FIG. 4C. The connector post 412 includes an elongate post 416. Defibrillation electrodes including connector posts such as that illustrated in FIG. 4C may be obtained from the Physio-Control Company. Also, the connector 100 is constructed to mate with a standard dot-type fastener 418 of a patient monitoring electrode 420 such as that illustrated in FIG. 4D.

The connector 100 includes a wire 102 for electrically coupling a connector assembly 104 to the defibrillator (not shown). As will be described in more detail below, the connector assembly 104 is constructed to permit the connector 100 to mate with the various connectors 402, 408, 412, and 418 illustrated in FIGS. 4A, 4B, 4C, and 4D, respectively.

The connector assembly 104 is mounted within a casing 106 wherein the casing has a cylindrical portion 108 and an elongated portion 110. The cylindrical portion 108 includes a back face 112, a substantially continuous side wall 114 and a recessed front face forming a body receiving chamber 116 into which is mounted the connector assembly 104. The cylindrical portion 108 further includes a flange 118 extending inwardly into the body receiving chamber 116 to define a groove 120 extending around the interior of the body receiving chamber 116 into which is positioned the connector assembly 104. The elongated portion 110 of the casing 106 also includes a cylindrical channel 122 for receiving the wire 102.

Figure 2:
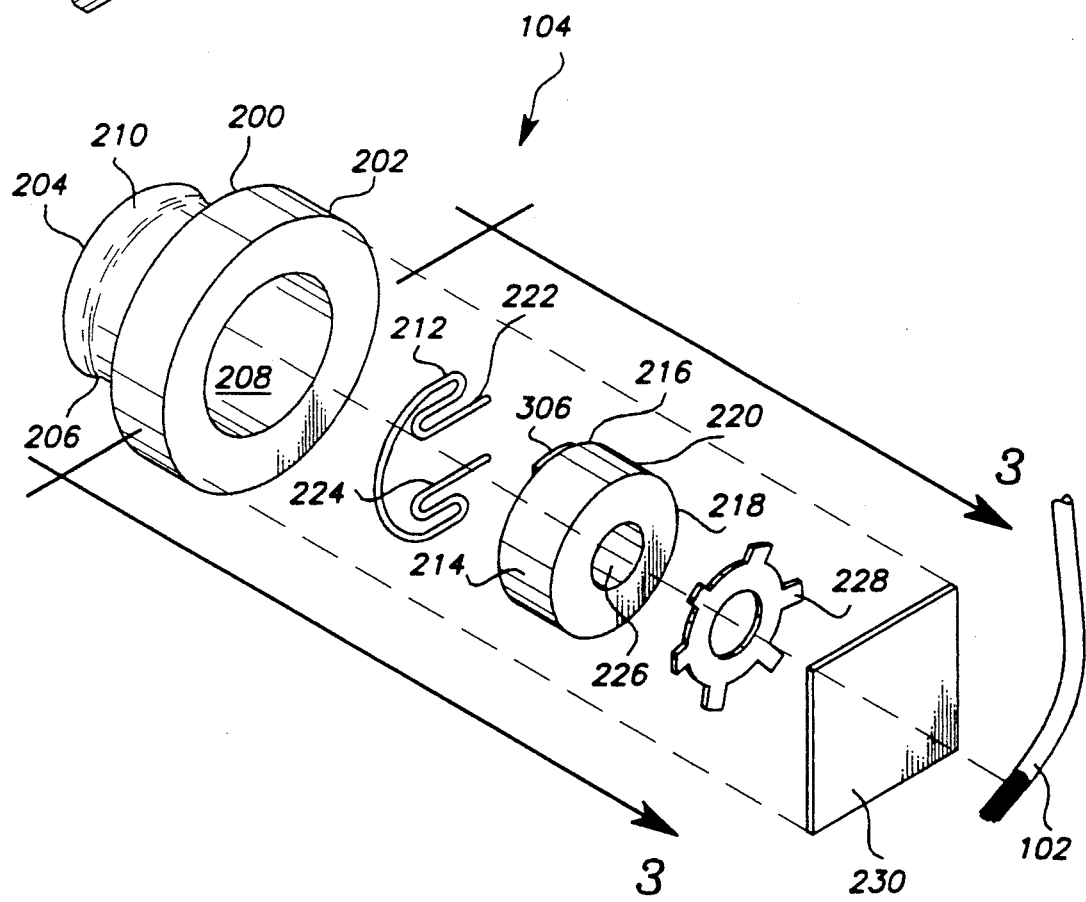
FIG. 2 is an exploded isometric view of the connector assembly illustrated in FIG. 1.
Figure 3:
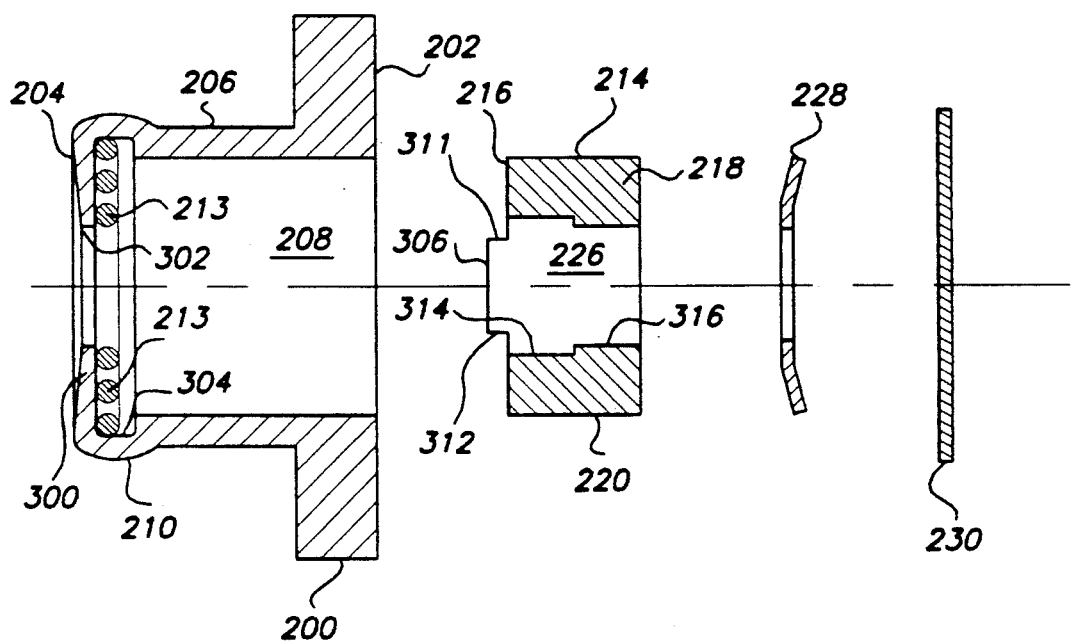
FIG. 3 is a cross-sectional view of the connector assembly illustrated in FIG. 1 taken along the line 3—3.

With reference to FIGS. 2 and 3 a more detailed description of the connector assembly 104 will be provided. The connector assembly 104 includes a body 200 constructed of a substantially conductive material. The body has a first, relatively large diameter cylindrical portion 202, and a second, relatively small diameter cylindrical portion 204. The first portion 204 has a cylindrical sidewall 206 with an outwardly projecting lip 210 formed at one end. The first portion 202 of the body 200 extends outward therefrom and is constructed to mate with the groove 120 (FIG. 1) of the casing 106 to fix the body to the casing so that the first portion 202 of the body 200 is proximate the back face 112 of the casing 106. As will become apparent to those skilled in the art, by securing the body 200 to the casing 106, the first portion 202 further secures the connector assembly 104 to the casing 106. The first and second portions 202 and 204 define a retainer chamber 208.

The lip 210 mates with a cup-type connector of a defibrillation electrode. More particularly, the lip 210 is constructed to mate with the cup-type connectors 404 and 408 illustrated in FIGS. 4A and 4B to mechanically secure the connector 100 to the respective defibrillation electrode. The second portion 204 further includes an inwardly extending flange 300 (best illustrated in FIG. 3) that defines an aperture 302 for receiving a post of the defibrillation electrode. The aperture 302 is constructed for receiving the post 406 and 416 of the defibrillation electrodes illustrated in FIGS. 4A and 4C, respectively. Still further, the aperture 302 is constructed for receiving the dot-type fastener 418 illustrated in FIG. 4D. Accordingly, the lip 210 and the flange 300 cooperate to permit the connector 100 to mechanically engage defibrillation electrodes having cup type connectors for securing the connector 100 to the defibrillation electrode while accommodating the stems of the connectors.

The flange 300 of the body 200 defines a groove 304 about the interior of the retainer chamber 208. The groove 304 receives a spring 213. Like the body 200, the spring 213 is constructed of a substantially conductive material so that electricity is conducted between the body 200 and the post by the spring 213. The spring 213 is positioned within the groove 304 for engaging a post of a defibrillation electrode to grip the post. More particularly, the spring 213 grips the post 406 and 416 of the defibrillation electrodes illustrated in FIGS. 4A and 4C, respectively. The spring 213 is further constructed for gripping the dot-type fastener 418 illustrated in FIG. 4D. Accordingly, the spring 213 and lip 210 cooperate to mechanically secure the connector 100 to the defibrillation electrode. Further, in absence of a cup type connector, the spring 213 is sufficient to secure the connector 100 to the defibrillation electrode.

The connector assembly 104 also includes a retainer 214 received in the retainer chamber 208 of the body 200. Like the spring 213 and the body 200, the retainer 214 is constructed of a substantially conductive material to conduct electrical signals from the body to the post of the defibrillation electrode. The retainer 214 has a first end 216 and a second end 218 with a substantially continuous side 220 intermediate the first and second ends. The first end 216 abuts the spring 213 mounted in the groove 304 of the body 200 to retain the retainer 214 in the retainer chamber 208.

Figure 4D:
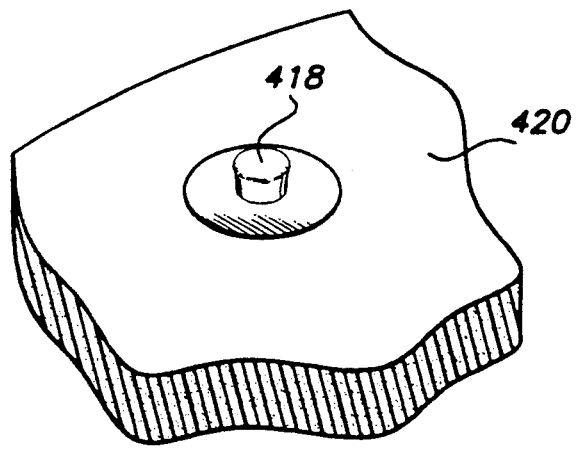

The first end 216 includes a first extending portion 306 (best illustrated in FIG. 3) and a second extending portion (not shown) positioned to extend outward from the retainer toward the protruding edge 300 when the retainer is mounted in the retainer chamber 208. The first extending portion 306 and the second extending portion (not shown) each engage the spring 213 to secure the spring to the groove 304 and to space the spring 213 for mating with a post of the defibrillation electrode. More particularly, the spring 213 includes first and second opposing spring portions 222 and 224 that engage the outer surfaces 311 and 312 of the extending portion 306 so that the outer surfaces 311 and 312 space the spring portions 222 and 224 to mate properly with the post 406 and 412 (FIGS. 4A and 4C, respectively) and the dot-type fastener 418 (FIG. 4D). The second extending portion (not shown) spaces the spring 213 in a manner similar to that described by reference to the first extending portion 306.

The retainer 214 also includes a post channel 226 extending from the first end 216 to the second end 218 of the retainer for receiving a post of the defibrillation electrode. The post channel 226 extends entirely through the retainer 214 to accommodate the extended post 416 of the defibrillation electrode illustrated in FIG. 4C. Further, the post channel 226 has dual diameters, having a first portion 314 proximate the first end 216 of the retainer and a second portion 316 proximate the second end 218 of the retainer wherein the first portion 314 is constructed of a diameter greater than that of the second portion 316. The dual diameter construction of the post channel 226 allows clearance to permit proper mating of the small post 406 illustrated in FIG. 4A while the decreased diameter of the second end 218 provides a close fit to enhance the security of the connection of the long post 416 illustrated in FIG. 4C.

The connector assembly 104 further includes a retainer ring 228 mating with the retainer chamber 208 of the body 200. When assembled, the spring 213 is positioned in the groove 304 with the retainer 214 positioned in the retainer chamber 208 to space the spring, as discussed above. The retainer ring 228 is positioned in the retainer chamber proximate the second end 218 of the retainer to secure the retainer in the retainer chamber.

A conductor plate 230 is fixed to the body 200 covering the retainer chamber 208 so that the spring 213, retainer 214, and retainer ring 228, is mounted within the retainer chamber 208, as discussed above. The wire 102 is then electrically coupled to the conductor plate 230 by any suitable means.

The above described connector assembly 104 is compatible with each of the connectors illustrated in FIGS. 4A, 4B, 4C, and 4D, for defibrillation and monitoring electrodes, as well as being compatible with other connectors of similar construction. Furthermore, the connector assembly 104 provides a secure connection that permits rotation of the casing 106 of the connector 100. Still further, the connector assembly 104 is easily and quickly connected and disconnected to the above described connectors. Also, connection and disconnection of the connector assembly 104 is accomplished without the need for excessive force.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A connector for coupling medical equipment to a defibrillation electrode wherein the defibrillation electrode is constructed to be electrically coupled to a patient so that electrical signals are transmitted between the patient and the medical equipment, said connector comprising:
    body means for receiving electrical signals from the medical equipment and for transferring electrical signals to the medical equipment, said body means including lip means for mating with a cup connector of the defibrillation electrode;
    spring means for engaging a post of the defibrillation electrode and for transferring electrical signals between the post and said body means, said body means including means for receiving and positioning said spring means so that said spring means is proximate the post when said connector is mounted to the defibrillation electrode;
    retainer means for retaining said spring means in said body means, said retainer means including channel means, extending through said retainer means, for receiving a post of the defibrillation electrode wherein said channel means has first and second portions and wherein the diameter of said first portion is greater than the diameter of said second portion; and
    casing means for receiving said body means, said spring means, and said retainer means, said casing means including means for conducting electrical signals between said body means and the medical equipment.

2. The connector as recited in claim 1 wherein said retainer means further includes first and second extending portions positioned to extend outward from said retainer means and constructed to engage said spring means to secure said spring means in said body means and to space said spring means for mating with a post of the defibrillation electrode.

3. The connector as recited in claim 1 wherein said body means further comprises a lip portion about the exterior of said body means for mating with a cup type connector of the defibrillation electrode.

4. A connector for coupling medical equipment to a defibrillation electrode wherein the defibrillation electrode is constructed to be electrically coupled to a patient so that electrical signals are transmitted between the patient and the medical equipment, said connector comprising:
    a plastic casing for housing the connector, said plastic casing having a casing first end and a casing second end, said casing first end having a back end and a substantially continuous casing side portion connected to said back end to define a body receiving chamber with an open end opposite said back end, said body side portion having a flange proximate said open end of said body receiving chamber to define a casing groove about the interior side of said body receiving chamber, said plastic casing further including a channel extending from said casing second end to said body receiving chamber of said first end;
    a body constructed of substantially conductive material, said body having a body first end and a body second end with a substantially continuous body side portion intermediate said body first and second ends to define a retainer chamber, said body first end including a rim portion extending outward therefrom and constructed to mate with said casing groove to fix said body to said casing with said body first end proximate said back end, said body second end including a lip portion about the exterior of said body side portion for mating with a cup type connector of the defibrillation electrode, said body second end further including an edge portion protruding inward from said body side portion to define a body aperture for receiving a post of the defibrillation electrode, said edge portion being constructed to define a body groove about the interior of said retainer chamber proximate said body second end;
    a spring positioned in said body groove for engaging a post of the defibrillation electrode to grip the post, said spring being constructed of a substantially conductive material so that electricity is conducted between said body and the post by said spring;
    a retainer sized to be received in said retainer chamber, said retainer having a retainer first end and a retainer second end with a substantially continuous retainer side intermediate said first and second ends, said retainer first end being constructed to abut said protruding edge of said body to retain said retainer in said retainer chamber, said retainer first end further including first and second extending portions positioned to extend outward from said retainer toward said protruding edge when said retainer is mounted in said retainer chamber and constructed to engage said spring to secure said spring in said body groove and to space said spring for mating with a post of the defibrillation electrode, said retainer further including a post channel extending from said retainer first end to said retainer second end for receiving a post of the defibrillation electrode, said retainer being constructed of a substantially conductive material to conduct electrical signals from said body to the post of the defibrillation electrode;

a retainer ring constructed to mate with said retainer chamber, said spring being positioned in said body groove with said retainer positioned in said retainer chamber to space said spring and said retainer ring being positioned in said retainer chamber proximate said retainer second end to secure said retainer in said retainer chamber; and conductor means, extending through said channel of said casing and being electrically coupled to said body for conducting electrical signals from the medical equipment to said casing.

* * * * *